United States Patent [19]

Röchling et al.

[11] 3,937,715
[45] Feb. 10, 1976

[54] CERTAIN DIFLUORODICHLOROETHYLDIAZOLE COMPOUNDS

[75] Inventors: Hans Röchling, Altenhain, Taunus; Peter Hartz, Eschborn, Taunus; Gerhard Hörlein, Frankfurt am Main, all of Germany

[73] Assignee: Hoechst Aktiengesellschaft, Frankfurt am Main, Germany

[22] Filed: June 20, 1974

[21] Appl. No.: 481,459

[30] Foreign Application Priority Data
June 23, 1973 Germany.............................. 2332000

[52] U.S. Cl.................. 260/306.8 D; 71/90; 71/92; 260/247.1 M; 260/247.2 A; 260/268 C; 260/293.67; 260/293.68; 260/294.8 D; 260/295 S; 260/307 G
[51] Int. Cl.$^2$................ C07D 285/12; C07D 271/10
[58] Field of Search. 260/306.8 D, 307 G, 247.1 M, 260/247.2 A, 268 C, 293.68, 293.67, 295 S, 294.8 D

[56] References Cited
UNITED STATES PATENTS

| | | | |
|---|---|---|---|
| 3,565,901 | 2/1971 | Cebalo.......................... | 260/306.8 D |
| 3,657,264 | 4/1972 | Rucker et al................. | 260/306.8 D |
| 3,784,555 | 1/1974 | Cebalo et al.................. | 260/307 G |

*Primary Examiner*—Richard J. Gallagher
*Attorney, Agent, or Firm*—Curtis, Morris & Safford

[57] ABSTRACT

Compounds of the formula

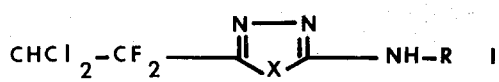

where X is oxygen or sulfur and R hydrogen, $(C_1-C_4)$-alkyl, $(C_1-C_3)$-acyl, $(C_1-C_2)$-halo -alkyl-carbonyl, $(C_2-C_6)$-alkoxy-alkyl-carbonyl, $(C_1-C_4)$-alkoxycarbonyl, phenyloxy-carbonyl, N-mono- or Di-$(C_1-C_4)$-alkyl-carbamoyl, N-$(C_1-C_4)$-alkyl-N-$(C_1-C_4)$-alkoxy-carbamoyl, N-phenyl-carbamoyl, the phenyl nucleus of which optionally being substituted by one or two halogen atoms and/or trifluormethyl groups; morpholino-carbonyl, N'-methylpiperazino-carbonyl, piperidino-carbonyl, pyrrolidino-carbonyl, N-(trihalogeno-phenoxy-sulfonyl)-carbamoyl or N-(1,1,3,3-tetrachloro-2-propoxy-sulfonyl)-carbamoyl, or, in the case of R being H or alkyl, also the physiologically tolerable salts thereof with inorganic or organic bases or acids.

2 Claims, No Drawings

CERTAIN DIFLUORODICHLOROETHYLDIAZOLE COMPOUNDS

The present invention relates to compounds of the formula

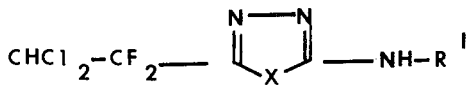

where X is oxygen or sulfur and R hydrogen, ($C_1$–$C_4$)-alkyl, ($C_1$–$C_3$)-acyl, ($C_1$–$C_2$)-halo-alkyl-carbonyl, ($C_2$–$C_6$)-alkoxy-alkyl-carbonyl, ($C_1$–$C_4$)-alkoxycarbonyl, phenyloxy-carbonyl, N-mono- or di-($C_1$–$C_4$)-alkyl-carbamoyl, N-($C_1$–$C_4$)-alkyl-N-($C_1$–$C_4$)-alkoxy-carbamoyl, N-phenyl-carbamoyl, the phenyl nucleus of which optionally being substituted by one or two halogen atoms and/or trifluoromethyl groups; morpholino-carbonyl, N'-methylpiperazino-carbonyl, piperidino-carbonyl, pyrrolidino-carbonyl, N-(trihalogeno-phenoxy-sulfonyl)-carbamoyl or N-(1,1,3,3-tetrachloro-2-propoxy-sulfonyl)-carbamoyl, or, in the case of R being H or alkyl, also the physiologically tolerable salts thereof with inorganic or organic bases or acids.

Preferred lower alkyl or alkoxy groups as cited above are those having 1 or 2 carbon atoms, preferred halogen atoms are F, Cl, Br, especially F and/or Cl. However, compounds preferred above all are those where R is hydrogen.

The compounds of formula I have a morphoregulative action in plants, they interfere with the physiological mechanisms of a plant and may therefore be used for regulation of plant growth.

By way of example the following compounds of formula I may be mentioned as growth regulators:
2-(1',1'-difluoro-2',2'-dichloroethyl)-5-amino-, -5-acetamido-, -5-trichloro-acetamido-, -5-dichloro-acetamido-, -5-chloro-acetamido-, -5-propionamido-, -5-α,α-dichloro-propionamido-, -5-ethoxy-carbonyl-amino, -5-isopropoxy-carbonylamino-, -5-N-methyl-carbamoylamino-, -5-morpholino-carbonylamino-, -5-N'-methylpiperazino-carbonylamino-, -piperidino-carbonylamino-, -pyrrolidino-carbonylamino-1,3,4-thiadiazole or -oxadiazole.

The compounds of formula I are prepared by reacting imido esters of the formula

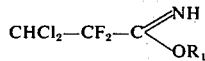

where $R_1$ is lower alkyl, with thiosemicarbazide, semicarbazide or a salt thereof, cyclizing the compounds of the formula

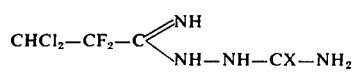

so obtained in the presence of a low molecular weight alcane-carboxylic acid to form compounds of the formula

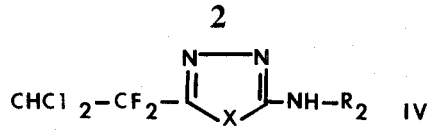

where $R_2$ is the acyl radical of the carboxylic acid used if X is S or hydrogen if X is O, optionally splitting off the radical $R_2$ by acidic saponification, and optionally converting the compounds of the formula

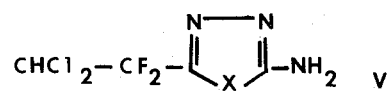

so obtained to compounds of formula I by alkylation or reaction with corresponding isocyanates or acid halides, or converting them with phosgene to the corresponding isocyanates and reacting the latter with corresponding secondary amines.

The compounds of formula II are known for example from Ann. Chim. 58 (1968), No. 1, pp. 25–31. Their reaction with semicarbazide or thiosemicarbazide may be carried out in polar solvents such as methanol, ethanol, propanol, isapropanol, acetone, methylethylketone, acetonitrile, dimethyl formamide, or dimethyl sulfoxide, but preferably in the presence of lower aliphatic carboxylic acids such as formic or acetic acid. When instead of the free semicarbazide or thiosemicarbazide, the salts thereof (preferably the hydrochlorides or sulfates) are used as starting substances, they have first to be converted to the free compounds. For this purpose, an at least equimolar amount of a basic agent such as sodium or potassium carbonate, pyridine or triethylamine is added to the salt in one of the cited polar solvents. The reaction temperatures are from 20° to 80°C, preferably from 30° to 60°C.

Cyclization to form the compounds of formula IV is carried out by heating to temperatures of from 70° to 140°C with organic acids such as formic, acetic or propionic acid. If starting compounds in which X is S are subjected to this cyclization, the acyl radical of the acid used is introduced into the free amino group of the cyclization product. For practical reasons, the preparation of the thiadiazoles generally starts from free thiosemicarbazide, and is carried out in an acidic medium, for example in glacial acetic acid. Proceeding in this manner, the intermediate compound of formula III in which X is S is first formed at low temperature; however, with increasing reaction temperature (for example to the boiling point of the solvent) compound III is cyclized in situ to compound IV (X = S, $R_2$ = low molecular weight alkanoyl).

By heating in inorganic acids, preferably sulfuric acid, or in mixtures of inorganic acids with organic solvents such as HCl/ethanol, the acyl radical is split off the thiadiazoles of formula IV, and the salts of the corresponding inorganic acid with the amine V are obtained. By reaction of the salts with bases such as NaOH, KOH or ammonium hydroxide, the free amine is obtained. The amines of formula V are then monoalkylated at the amino group in known manner (using for example diazomethane or dimethyl sulfate) or reacted with acid halides (preferably acid chlorides) or isocyanates to form the compounds of formula I. It is furthermore possible to convert the amino group of the compounds V to the —N=C=O group with phosgene and subsequently react the latter group with open-chain or cyclic secondary amines.

The compounds of formula V may be converted, if desired to their salts by means of inorganic or organic acids or bases, whereby the thiadiazoles of formula V are more basic than the oxadiazoles. Suitable acids are for example HCl, $H_2SO_4$, $H_3PO_4$, $HClO_4$, formic or acetic acid; suitable bases are for example $NaOCH_3$, NaOH, KOH, $NH_3$, $N(CH_3)_3$, or pyridine.

The compounds have a broad utility as growth depressing agents in crop plants and leguminosae as well as in weed grasses and broad-leaf weeds. Especially important is their utility in barley, for which no suitable growth regulator is hitherto known. Spring or winter barley is especially susceptible to flattening, which can be prevented by controlling the longitudinal growth by means of the invention compounds. The compounds of the invention are applied either in the pre-emergent or, preferably, the post-emergent phase, especially in the period between three-leaf stage and sprouting, and above all in the period of tillering, and shortly before sprouting.

The growth reduction of the plant does not cause any damage such as decoloration, stunting or withering. On the contrary, the compounds of formula I, when applied to broadleaf plants, cause an increased branching of the treated plants, that is, the so-called "sleeping eyes" are incited to sprout.

Since besides the growth-retarding activity in crop plants, a considerable growth reducation of weed grasses and weeds can also be observed, the substances of the invention may be applied also to areas where vegetation is desired, for example in order to combat erosion, but is to be kept as low as possible. The stem-shortening activity of the substances of the invention in the pre- and post-emergent phase may be also utilized in combination with pre- and post-emergence herbicides and/or fertilizers. This combined application is advantageous for example in cereals, since the farmer may join the spraying of herbicide and stem-shortening product in one single operation and thus save considerable time and cost.

The compounds of the invention may be prepared in usual admixture with solid or liquid formulation additives such as inert carrier materials, adhesives, wetting or dispersing agents or grinding auxiliaries, in the form of wettable powders, emulsions, suspensions or dusting powders, the active substance concentration of which being from 5 to 80 %.

As carrier material for solid products, mineral substances, for example aluminium silicates, argillaceous earths, kaolin, chalks, siliceous chalks, talcum, kieselgur or hydrated silicic acids can be used, or preparations of these mineral substances with special additives, for example, chalk with sodium stearate. As carrier material for liquid preparations, any suitable organic solvents may be employed, for example toluene, xylene, diacetone alcohol, isophorone, gasolines, paraffin oils, dioxan, dimethyl formamide, dimethyl sulfoxide, ethyl or butyl acetate, tetrahydrofuran, chlorobenzene, or similar substances.

Suitable adhesives are glue-like cellulose products or polyvinyl alcohols.

As wetting agents, any suitable emulsifiers may be used, for example ethoxylated alkylphenols, salts of aryl- or alkyl-aryl-sulfonic acids, salts of ethoxylated benzenesulfonic acids, or soaps.

Suitable dispersing agents are cellulose pitch (salts of ligninsulfonic acid), salts of naphthalenesulfonic acid or sometimes, hydrated silicic acids or kieselguhr.

As grinding auxiliaries, suitable inorganic or organic salts, for example sodium sulfate, ammonium sulfate, sodium carbonate and sodium bicarbonate, sodium thiosulfate, sodium stearate, or sodium acetate may be used.

The following examples illustrate the invention.

A. Examples of preparation

EXAMPLE 1a:

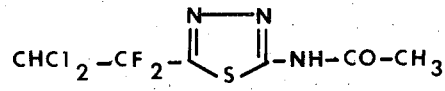

910 g (10 mols) of thiosemicarbazide were suspended in 10 liters of pure glacial acetic acid, and 1.92 g (10 mols) of α,α-difluoro-β,β-dichloro-imido-propionic acid methyl ester were added dropwise in such a manner that the reaction temperature did not exceed 32°C. Agitation was then continued for a further 3 hours at 30°C. The batch was slowly heated to 50°C, and agitation was continued at this temperature for a further 5 hours. Subsequently, in order to cyclize the $N_1$-thiocarbamoyl-(α,α-difluoro-β,β-dichloro)-propionamidrazone (melting point 157°–158°C) obtained, the batch was refluxed for 7 hours with agitation. After cooling to room temperature, water was added until a solid precipitated which was suction-filtered and washed with water.

After drying, 1710 g (62 %) of 2-(1′,1′-difluoro-2′,-2′-dichloroethyl)-5-acetamido-1,3,4-thiadiazole were obtained. A sample was recrystallized from toluene: melting point 182°–184°C.

EXAMPLE 1b:

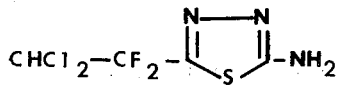

1580 g of 2-(1′,1′-difluoro-2′,2′-dichloro-ethyl)-5-acetamido-1,3,4-thiadiazole were mixed with 5700 ml of concentrated $H_2SO_4$ and heated to 120°–130°C for 2 hours with ageitation. After cooling, the sulfuric acid containing solution was poured into icewater while stirring and neutralized with 30 % sodium hydroxide solution. The precipitate formed was separated and washed with water. After drying, 1320 g (98.5 %) of 2-(1′,1′-difluoro-2′,2′-dichloro-ethyl)-5-amino-1,3,4- thiadiazol having a melting point of 181°–182°C were obtained.

EXAMPLE 2a:

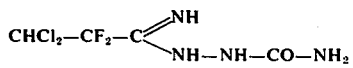

192 g (1 mol) of α,α-difluoro-β,β-dichloro-imidopropionic acid methyl ester were dissolved in 625 ml of methanol, 69 g (0.5 mol) of pulverulent potassium carbonate were added as well as, dropwise, a solution of 111.5 g (1 mol) of semicarbazide hydrochloride in 350 ml of water, which caused the temperature to rise to 31°C. Agitation was continued for 1 hour without external heating, and then for 4 hours at a temperature of 55°C. The batch was then allowed to cool, and the potassium chloride formed was removed by suction-filtration. The filtrate was concentrated, the residue was treated with 4 liters of carbon tetrachloride with heating; the undissolved residual potassium chloride was removed by decanting. The reaction product crystallized, and 206 g (87.8 %) of $N_1$-carbamoyl-(α,α-difluoro-β,β-dichloro)-propionamidrazone having a melting point of 105°C were obtained.

EXAMPLE 2b:

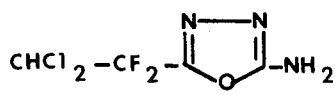

25 g (0.15 mol) of $N_1$-carbamoyl-(α,α-difluoro-β,β-dichloro)-propionamidrazone were dissolved in 200 ml of glacial acetic acid and refluxed for 6 hours. Subsequently, the batch was concentrated, the residue was stirred with methylene chloride, the solid formed was suction-filtered, washed with water and dried.

16.4 g of 2-(1',1'-difluoro-2',2'-dichloro-ethyl)-5-amino-1,3,4-oxadiazole having a melting point of 171°C were obtained.

EXAMPLE 3:

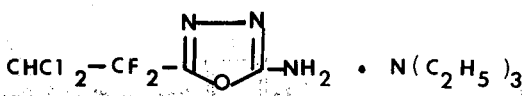

43.5 g (0.2 mol) of 2-(1',1'-difluoro-2',2'-dichloroethyl)-5-amino-1,3,4-oxadiazole were dissolved in 400 ml of acetonitrile, and 27.8 ml (0.2 mol) of triethylamine were added, which caused the temperature to rise from 20° to 35°C. A colorless solid precipitated. Agitation was continued for one-half hour at 60°C, the batch was allowed to cool, the residue was suction-filtered and washed with water. After recrystallization from dioxan, 43.8 g (68.6 %) of the salt of 2-(1',1'-difluoro-2',2'-dichloro-ethyl)-5-amino-oxadiazoltriethylamine were obtained having a melting point of 163°–164°C.

EXAMPLE 4:

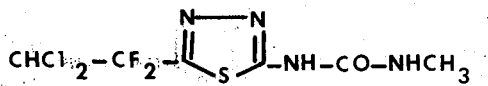

23.4 g (0.1 mol) of 2-(1',1'-difluoro-2',2'-dichloroethyl)-5-amino-1,3,4-thiadiazol were suspended in 550 ml of methylene chloride, and 11.7 ml (0.2 mol) of methylisocyanate were added, which caused the temperature of the mixture to rise from 26° to 30°C. A solution was obtained, which was allowed to cool with agitation and, after being abandoned for 24 hours, was concentrated at room temperature. The solid residue was recrystallized from toluene. 26.75 g (92 %) of 2-(1',1'-difluoro-2',2'-dichloro-ethyl)-5-N-methylcarbamoyl-amino-1,3,4-thiadiazole having a melting point of 187°C were obtained.

The compounds listed in Table I were prepared in an analogous manner.

Table I

| Example No. | Formula ($R_3$=—$CF_2$—$CHCl_2$) | melting point °C |
|---|---|---|
| 5 | $R_3$-[thiadiazole]-NH-CO-NH-[C₆H₃Cl₂] | 248–249 |
| 6 | $R_3$-[thiadiazole]-NH-CO-NH-$C_4H_9$ | 135–137 |
| 7 | $R_3$-[thiadiazole]-NH-CO-NH-$C_2H_5$ | 148–150 |
| 8 | $R_3$-[thiadiazole]-NH-CO-NH-$C_3H_7$ | 135–136 |

Table I-continued

| Example No. | Formula (R₃=—CF₂—CHCl₂) | melting point °C |
|---|---|---|
| 9 | R₃-[thiadiazole]-NH—CO—NH—SO₂—O—CH(CHCl₂)₂ | non-distillable oil |
| 10 | R₃-[thiadiazole]-NH—CO—NH—SO₂—O—[2,4,6-trichlorophenyl] | 60–61 |
| 11 | R₃-[thiadiazole]-NH—CO—NH—[3,5-bis(CF₃)phenyl] | 230 |
| 12 | R₃-[oxadiazole]-NH—CO—NH—[3,4-dichlorophenyl] | 210 |
| 13 | R₃-[oxadiazole]-NH—CO—NHCH₃ | non-distillable oil |

EXAMPLE 14:

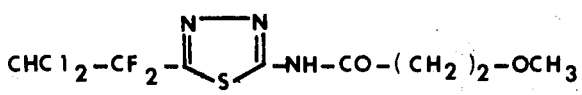

23.4 g (0.1 mol) of 2-(1',1'-difluoro-2',2'-dichloroethyl)-5-amino-1,3,4-thiadiazole were dissolved at 80°C in 700 ml of dried toluene, 13.9 ml of triethylamine were added, and dropwise at the same temperature 12.25 g (0.1 mol) of β-methoxypropionic acid chloride. Agitation was continued for 5 hours at 100°C. The batch was allowed to cool, the hydrochloride formed was suction-filtered and the filtrate was concentrated. The residue was recrystallized from petroleum ether (boiling point 80°–110°C).

Yield: 20.4 g (64 %) of 2-(1',1'-difluoro-2',2'-dichloroethyl)-5-(β-methoxy-propionamido)-1,3,4-thiadiazole having a melting point of 112°–113°C.

In an analogous manner, the compounds listed in Table II were prepared.

Table II

| Example No. | Formula (R₃ = —CF₂—CHCl₂) | melting point °C |
|---|---|---|
| 15 | R₃-[thiadiazole]-NH—CO—CH₂—O—C₄H₉ | 84 |
| 16 | R₃-[thiadiazole]-NH—CO—CF₃ | 105–107 |

Table II-continued

| Example No. | Formula ($R_3 = -CF_2-CHCl_2$) | melting point °C |
|---|---|---|
| 17 | $R_3-\underset{S}{\overset{N-N}{\vert\vert}}-NH-COOC_2H_5$ | 116–118 |
| 18 | $R_3-\underset{S}{\overset{N-N}{\vert\vert}}-NH-CO-CH_2Cl$ | 158–159 |
| 19 | $R_3-\underset{S}{\overset{N-N}{\vert\vert}}-NH-COO-C_6H_5$ | 130–131 |
| 20 | $R_3-\underset{S}{\overset{N-N}{\vert\vert}}-NH-COO-C_4H_9$ | 98–99 |
| 21 | $R_3-\underset{O}{\overset{N-N}{\vert\vert}}-NH-COO-C_2H_5$ | 163 |

EXAMPLE 22a:

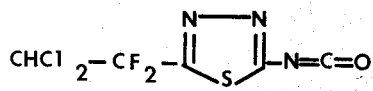

21.7 g (0.1 mol) of 2-(1′,1′-difluoro-2′,2′-dichloroethyl)-5-amino-1,3,4-thiadiazole were suspended at room temperature in 500 ml of chlorobenzene, and a solution of 30 g of phosgene in 200 ml of chlorobenzene was rapidly added with agitation. With further agitation and feeding-in of gaseous phosgene, the temperature was raised by 15°C per hour until 110°C were attained (a clear solution was obtained from 60°C onward). The solution was then allowed to cool, nitrogen was passed through the solution to remove the residual phosgene, and the solution was concentrated. A brittle mass remained which became pulverulent on trituration with petroleum ether (boiling point 80°–110°C). By suction-filtration and drying, 19 g (73 %) of 2-(1′,-1′-difluoro-2′,2′-dichloro-ethyl)-5-isocyanato-1,3,4-thiadiazole were obtained. Decomposition temperature: 200°C.

EXAMPLE 22b:

26.0 g (0.1 mol) of 2-(1′,1′-difluoro-2′,2′-dichloroethyl)-5-isocyanato-1,3,4-thiadiazole were dissolved in 700 ml of methylene chloride, and 17.4 g (0.2 mol) of morpholine (distilled over NaOH) were added dropwise, which caused the temperature to rise from 27° to 34°C. Agitation was continued at 35°C for 4 hours, and the batch was then allowed to cool. After concentration, a solid residue was obtained which was recrystallized from toluene.
Yield: 25.5 g (73.5 %) of 2-(1′,1′-difluoro-2′,2′-dichloroethyl)-5-morpholine-carbonamido-1,3,4-thiadiazole, melting point 194°C.

In an analogous manner, the compounds listed in Table III were prepared.

Table III

| Example No. | Formula ($R_3 = -CF_2-CHCl_2$) | melting point °C |
|---|---|---|
| 23 | $R_3-\underset{S}{\overset{N-N}{\vert\vert}}-NH-CO-N(CH_3)_2$ | 168–169 |

Table III-continued

| Example No. | Formula ($R_3 = -CF_2-CHCl_2$) | melting point °C |
|---|---|---|
| 24 | $R_3-\underset{S}{\underset{\|}{C}}\overset{N-N}{\underset{\|}{C}}-NH-CO-N\begin{subarray}{l}C_2H_5\\C_2H_5\end{subarray}$ | 90 |
| 25 | $R_3-\underset{S}{\underset{\|}{C}}\overset{N-N}{\underset{\|}{C}}-NH-CO-N\begin{subarray}{l}CH_3\\O-CH_3\end{subarray}$ | 102–105 |

EXAMPLE 26:

Preparation of a 20 % wettable powder
 12 g of active substance according to Example 1b were preground with
 3 g of Silcasil, and subsequently mixed in a turbine mixer with
 45 g of a preliminary mixture prepared by mixing
 10 g of cellulose pitch
 49 g of Sillitin Z
 8 g of Silcasil
 7 g of Polypropyleneglycol P 750 + Silcasil = 1:1
 1 g of Hostapon.

In this manner, 60 g of a 20 % wettable powder were obtained.

B. Examples of application

EXAMPLE I:

Plants of cereals (wheat, barley, oats and rye) in the 2- to 3-leaf stage were sprayed with aqueous suspensions of substances of the invention.

Table I shows the stem-shortening effect; the growth decrease (GD) being expressed in percent as compared to untreated plants. As comparative substance, in this and the following tests, the known commercial product chlorocholin chloride was used.

Table I

Greenhouse test, post-emergence

Growth decrease (GD) in % compared to untreated cereals (spring wheat and barley, oats, spring rye)

| Preparation according to Example | Doses kg/ha of active substance | Spring wheat GD % | Spring barley GD % | Oats GD % | Spring rye GD % |
|---|---|---|---|---|---|
| 2b | 5.0 | 45 | 35 | 30 | 25 |
|  | 1.25 | 10 | 10 | 10 | 10 |
|  | 0.3 | 10 | 0 | 0 | 5 |
| 1b | 5.0 | 15 | 15 | 10 | 10 |
|  | 1.25 | 10 | 10 | 5 | 5 |
|  | 0.3 | 10 | 0 | 0 | 0 |
| chlorocholine chloride | 5.0 | 35 | 0 | 10 | 0 |
|  | 1.25 | 10 | 0 | 5 | 0 |
|  | 0.3 | 10 | 0 | 5 | 0 |

EXAMPLE II:

Broad-leaf plants such as rape, dwarf-bush bean, soybean and horse bean in the 2- to 3-leaf stage were sprayed with aqueous suspensions of substances of the invention. The results of these tests are listed in Tables IIa and IIb expressed in percent of growth decrease (GD) as compared to untreated control plants.

TABLE IIa

Greenhouse test, post-emergence

Growth decrease (GD) in % compared to untreated plants (rape, dwarf-bush bean, soybean, horse bean).

| Preparation according to Example | Doses kg/ha of active substance | Rape GD % | Dwarf-bush bean GD % | Soy-bean GD % | Horse bean GD % |
|---|---|---|---|---|---|
| 2b | 5.0 | 70 | 55 | 70 | 50 |
|  | 1.25 | 20 | 50 | 40 | 30 |
|  | 0.3 | 0 | 0 | 0 | 0 |
| 1b | 5.0 | 10 | 5 | 40 | 45 |
|  | 1.25 | 10 | 5 | 10 | 20 |
|  | 0.3 | 0 | 0 | 0 | 15 |
| chlorocholine chloride | 3.0 | 10 | 30 | 15 | 5 |
|  | 1.25 | 0 | 10 | 0 | 0 |
|  | 0.3 | 0 | 0 | 0 | 0 |

TABLE IIb

Greenhouse test, post-emergence

Growth decrease (GD) in % compared to untreated plants (dwarf-bush bean, horse bean, soybean).

| Preparation according to Example | Dose kg/ha of active substances | Dwarf-bush bean GD % | Horse bean GD % | Soy-bean GD % |
|---|---|---|---|---|
| 3 | 2.5 | 20 | 40 | 40 |
|  | 0.6 | 10 | 10 | 10 |
|  | 0.15 | 0 | 0 | 0 |
| chlorocholine chloride | 2.5 | 15 | 0 | 5 |
|  | 0.6 | 0 | 0 | 0 |
|  | 0.15 | 0 | 0 | 0 |

EXAMPLE III:

Weeds and weed grasses of different growth stages were sprayed with the substances of the invention. The results are listed in Tables IIIa and IIIb showing the growth decrease in percent as compared to untreated plants.

TABLE IIIa

Greenhouse test, post-emergence

Growth decrease (GD) of weeds in % compared to untreated control plants. The preparation were applied to the test plants in stage C and $D_2$
stage C = 1 pair of leaves has developed
stage $D_2$ = 2 pair of leaves or of leaf stipules have developed.

| Preparation according to Example | Dose kg/ha of active substance | Galium aparine GD % C | Galium aparine GD % $D_2$ | Stellaria media GD % C | Stellaria media GD % $D_2$ | Sinapis arvensis GD % C | Sinapis arvensis GD % $D_2$ |
|---|---|---|---|---|---|---|---|
| 2b | 5.0 | 25 | 50 | 90 | 80 | 80 | 45 |
|  | 1.25 | 20 | 15 | 70 | 40 | 50 | 15 |
|  | 0.3 | 0 | — | 20 | 0 | 10 | 0 |
| 22b | 5.0 | 20 | 10 | 60 | 10 | 45 | 25 |
|  | 1.25 | 10 | 5 | 10 | 5 | 25 | 10 |
|  | 0.3 | 5 | 0 | 0 | 0 | 10 | 0 |
| chlorocholine chloride | 5.0 | 0 | 10 | 0 | 0 | 45 | 20 |
|  | 1.25 | 0 | 0 | 0 | 0 | 40 | 15 |
|  | 0.3 | 0 | 0 | 0 | 0 | 20 | 10 |

Table IIIb

Greenhouse test, post-emergence

Growth decrease (GD) of weeds in % compared to untreated control plants. The preparations were applied to the test plants in stage C and D; stage C=2 leaves; stage D = 3 leaves.

| Preparation according to Example | Doses kg/ha of active substance | Lolium multiflorum GD % C | Lolium multiflorum GD % D | Poa trivialis GD % C | Poa trivialis GD % D | Poa annua GD % C | Poa annua GD % D |
|---|---|---|---|---|---|---|---|
| 2b | 5.0 | 20 | 15 | 50 | 10 | 30 | 15 |
|  | 1.25 | 10 | 0 | 10 | 0 | 10 | 10 |
|  | 0.3 | 0 | 0 | 0 | 0 | 0 | 0 |
| chlorocholine chloride | 5.0 | 0 | 10 | 0 | 0 | 45 | 20 |
|  | 1.25 | 0 | 0 | 0 | 0 | 40 | 15 |
|  | 0.3 | 0 | 0 | 0 | 0 | 20 | 10 |

EXAMPLE IV:

The substance of the invention was tested in the field in lot and logarithmic tests. When the substance was applied to spring wheat having reaching a considerable growth already, a distinctive shortening of the stem was observed at an application rate of 2.0 kg/ha of active substance. With different spring wheat kinds this shortening amounted to 7.3 % on the average, the lower and upper limits were 4.2 to 11.4 %. When applying an amount of 1.0 kg/ha of active substance, there was only a 2.1 % effect (limits 0.8 to 3.5 %).

The results of the post-emergence spraying of different spring wheat kinds are listed in Table IV.

TABLE IV

Field test, post-emergence

Stem shortening (GD) of 3 spring wheat kinds in % compared to untreated plants.

| Preparation according to Example | Doses kg/ha of active substance | Janus GD % | Kolibri GD % | Opal GD % |
|---|---|---|---|---|
| 2b | 1.0 | 0.8 | 3.5 | 2.0 |
|  | 2.0 | 4.2 | 11.4 | 7.4 |

EXAMPLE V:

Besides the post-emergence effect, the pre-emergence activity of the substances of the invention was tested also in a greenhouse. The result was a considerable activity in monocotyledoneous and dicotyledoneous plants, the results being listed in the following Tables Va and Vb.

Table Va

Greenhouse test, pre-emergence

| Preparation according to Example | Dose kg/ha of active substance | Spring barley GD % | Oats GD % | Spring rye GD % |
|---|---|---|---|---|
| 2b | 2.5 | 10 | 10 | 5 |
|  | 0.6 | 5 | 5 | 5 |
|  | 0.15 | 0 | 0 | 0 |
| chlorocholine chloride | 2.5 | 10 | 0 | 5 |
|  | 0.6 | 0 | 0 | 5 |
|  | 0.15 | 0 | 0 | 0 |

Table Vb shows the pre-emergence effect on broad-leaf crop plants.

Table Vb

Field test, post-emergence

Growth decrease (GD) of dwarf-bush bean, horse bean and soybean in % compared to untreated control plants.

| Preparation according to Example | Dose kg/ha to active substance | Dwarf-bush bean GD % | Horse bean GD % | Soybean GD % |
|---|---|---|---|---|
| 2b | 2.5 | 35 | 15 | 50 |
|  | 0.6 | 10 | 0 | 0 |
|  | 0.15 | 0 | 0 | 0 |
| chlorocholine chloride | 2.5 | 10 | 0 | 0 |
|  | 0.6 | 0 | 0 | 0 |
|  | 0.15 | 0 | 0 | 0 |

What is claimed is:
1. Compounds of the formula

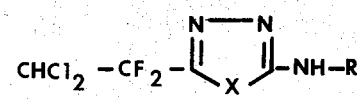

where X is oxygen or sulfur and R hydrogen, $(C_1-C_4)$-alkyl, $C_1-C_3$-alkanoyl, $(C_1-C_2)$-halo-alkyl-carbonyl, $(C_2-C_6)$-alkoxy-alkyl-carbonyl, $(C_1-C_4)$-alkoxycarbonyl, phenyloxy-carbonyl, N-mono- or di-$(C_1-C_4)$-alkyl-carbamoyl, N-$(C_1-C_4)$-alkyl-N-$(C_1-C_4)$-alkoxy-carbamoyl, N-phenyl-carbamoyl, the phenyl nucleus of which optionally being substituted by one or two halogen atoms and/or trifluoromethyl groups; morpholino-carbonyl, N'-methylpiperazino-carbonyl, piperidino-carbonyl, pyrrolidino-carbonyl, N-(trihalogeno-phenoxy-sulfonyl)carbamoyl or N-(1,1,3,3-tetrachloro-2-propoxy-sulfonyl)carbamoyl, or, in the case of R being H or alkyl, also the physiologically tolerable salts thereof.

2. Compounds of the formula

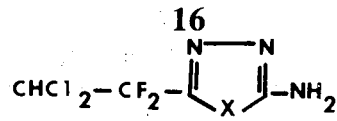

where X is oxygen or sulfur, or the physiologically tolerable salts thereof.

* * * * *